United States Patent [19]

Tsuji et al.

[11] 4,226,769
[45] Oct. 7, 1980

[54] PROCESS FOR PREPARING A SOLID PREPARATION OF A PENICILLIN DERIVATIVE

[75] Inventors: Terutsugu Tsuji; Shigeji Sato, both of Osaka; Keiji Fujioka, Amagasaki; Yoshiya Yamahira; Tadao Maeda, both of Osaka, all of Japan

[73] Assignee: Sumitomo Chemical Company, Limited, Osaka, Japan

[21] Appl. No.: 961,841

[22] Filed: Nov. 17, 1978

[30] Foreign Application Priority Data

May 8, 1978 [JP] Japan .................................. 53/54804

[51] Int. Cl.² .......................................... C07D 499/68
[52] U.S. Cl. .................................. 260/239.1; 424/256
[58] Field of Search ...................... 260/239.1; 424/256

[56] References Cited

U.S. PATENT DOCUMENTS 3,864,329  2/1975  Tobiki et al. ...................... 260/239.1
4,029,804  6/1977  Clark et al. ............................ 424/271

OTHER PUBLICATIONS

Remington's Practice of Pharmacy, pp. 155-156 (12th ed., 1961).
Kirk-Othmer, "Encyclopedia of Chemical Technology", vol. 7, pp. 368-370 (2nd ed., 1966).

Primary Examiner—Norman Morgenstern
Assistant Examiner—Vera C. Clarke
Attorney, Agent, or Firm—Birch, Stewart, Kolasch & Birch

[57] ABSTRACT

A process for freeze-drying a penicillin derivative of the formula:

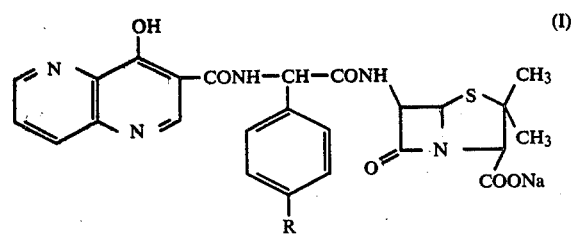

wherein R is a hydrogen atom or a hydroxyl group, by evaporating a frozen aqueous solution of the penicillin derivative (I) under vacuum from the frozen state to dryness, which is characterized by maintaining the temperature of the frozen solution within a range from the eutectic point of the solution determined by the electric resistance method to −8° C. when the penicillin derivative of the formula (I) wherein R is a hydrogen atom is to be freeze-dried, or −10° C. when the penicillin derivative of the formula (I) wherein R is a hydroxyl group is to be freeze-dried during the primary drying period of the drying process.

5 Claims, No Drawings

PROCESS FOR PREPARING A SOLID PREPARATION OF A PENICILLIN DERIVATIVE

The present invention relates to a process for preparing a solid preparation of a penicillin derivative. More particularly, it relates to a process for freeze-drying an aqueous solution of a penicillin derivative of the formula:

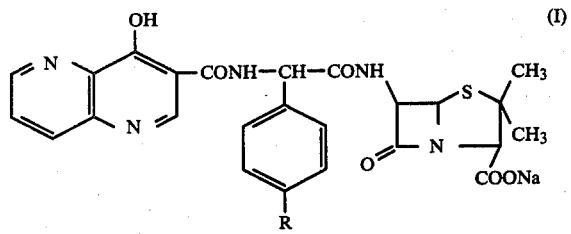

wherein R is a hydrogen atom or a hydroxyl group.

The penicillin derivative of the formula (I) has recently been developed and is known to be useful as an antimicrobial agent (cf. U.S. Pat. Nos. 3,594,733 and 3,864,329).

In developing the penicillin derivative (I) as an antimicrobial agent, it has been found that the most practical method for preparing an injection thereof is to dispense the penicillin derivative (I) in a dry state in a suitable container by a freeze-dry process; i.e. freezing an aqueous solution of the penicillin derivative (I) in a container and then drying it under vacuum from the frozen state.

It is known, however, that a freeze-drying process, especially the drying operation, is very time-consuming and therefore has to be conducted at the highest possible temperature to minimize the time required for completion of the drying.

It is also known that the drying operation may be divided into two parts; namely, the primary drying, which is the major part of the drying operation, and the secondary drying. During the primary drying, the temperature of the solution to be freeze-dried has to be maintained below its eutectic point since otherwise it melts. For example, in the case of carbenicillin and sulbenicillin, each of which has a similar chemical structure to the penicillin derivative (I) of the invention, an aqueous solution of the former has an eutectic point of −30° C. and that of the latter has an eutectic point of −29° C., when measured by the electric resistance method using a 10 w/v % solution. They melt immediately when the temperature rises over the eutectic point during the primary drying period and, because of this, they can not successfully be freeze-dried at a temperature over the eutectic point thereof. Thus, it is generally recognized that the eutectic point is the upper temperature limit of the primary drying period for a freeze-drying process of a penicillin aqueous solution. For this purpose, eutectic points are usually measured by the electric resistance method in which the temperature where the maximum change (drop) in electric resistance of a sample mixture is observed (hereinafter referred to as "MERC-point") is regarded as the eutectic point of the sample mixture.

It has now been found that a frozen aqueous solution of the penicillin derivative (I) of the invention does not melt even if the primary drying is conducted at a much higher temperature than its eutectic point determined by said method, more specifically its MERC-point.

Thus, an aqueous solution of the penicillin derivative (I) may be freeze-dried at a much higher temperature than its eutectic point.

When determined by said method, a 10 w/v % aqueous solution of sodium 6-[D-α-(4-hydroxy-1,5-naphthyridine-3-carboxamido)-2-phenylacetamido]penicillanate (hereinafter referred to as "Compound A") shows an eutectic point of −32° C., but an aqueous solution of Compound A does not melt even if the primary drying is conducted at a much higher temperature than the eutectic point. The upper temperature limit for the primary drying period of a freeze-drying process of an aqueous solution of Compound A is found to be −8° C.

Similarly, a 10 w/v % aqueous solution of sodium 6-[D-α-(4-hydroxy-1,5-naphthyridine-3-carboxamido)-2-(p-hydroxyphenyl)acetamido]penicillanate (hereinafter referred to as "Compound B") has an eutectic point of −30° C., but an aqueous solution of Compound B does not melt even if the primary drying is conducted at a higher temperature than the eutectic point. The maximum temperature limit for the primary drying period of the freeze-drying process of an aqueous solution of Compound B is −10° C.

Accordingly, the present invention provides a process for freeze-drying an aqueous solution of the penicillin derivative (I) which comprises drying said solution from the frozen state at a temperature ranging from the eutectic point of the solution to said upper temperature limit, i.e. −8° C. when an aqueous solution of Compound A is to be freeze-dried, or −10° C. when an aqueous solution of Compound B is to be freeze-dried.

In the present invention, the freeze-drying process can be carried out by freezing an aqueous solution of the penicillin derivative (I) in a suitable container in a per se conventional manner and then evaporating it under vacuum from the frozen state to dryness within said temperature range. The solution may preferably be frozen by cooling it at a temperature a little lower than around −40° C. for about one to two hours. The frozen solution is then subjected to a drying operation under high vacuum (e.g. 0.1 − 0.01 torr) in a per se conventional manner. During the primary drying period, the temperature of the solution is maintained within said temperature range by adjusting the temperature of the shelves of the freeze-drying unit, preferably while reducing the vacuum to some extent (e.g. 0.2 − 0.1 torr). After completion of the primary drying, the temperature is slowly raised to a temperature of about 20° to 50° C. as the evaporation is completed. The concentration of Compound A in the solution may vary from 5 w/v % to 12.5 w/v % and the concentration of Compound B may vary from 5 w/v % to 30 w/v %.

By the present invention, it has become possible to accomplish the freeze-drying process of the penicillin derivative (I) in a much shorter period of time, compared with the case where the freeze-drying process is conducted in a conventional manner.

The following examples are given to illustrate the present invention more precisely, but it is not intended to limit the present invention thereto.

EXAMPLE 1

An aqueous solution of Compound A was freeze-dried in accordance with the following procedure:

Three ml of about 10 w/v % aqueous solution of Compound A was poured into a vial (8 ml in volume; 21 mm in outer diameter; 40 mm in height). The solution in the vial was transferred to the shelf in the freeze-drying unit and frozen by cooling it at a temperature a little lower than −40° C. for 1½ hours. The frozen solution was then dried under vacuum (0.1–0.01 torr) at the temperature as given in the table below. The temperature of the solution was controlled by adjusting the temperature of the shelf.

The results are given in the following Table:

| Experiment No. | Temperature of the solution (°C.) | Time required for completion of the drying | State of the dried Compound A |
|---|---|---|---|
| 1 | −32 | 2 days | well dried |
| 2 | −25 | 1 day | well dried |
| 3 | −20 | 1 day | well dried |
| 4 | −15 | 1 day | well dried |
| 5 | −10 | 1 day | well dried |
| 6 | −6 | The solution melted during the drying process. | |

EXAMPLE 2

An aqueous solution of Compound A was freeze-dried in accordance with the following procedure:

Eight ml of about 7.5 w/v % aqueous solution of Compound A was poured into a vial (18 ml in volume; 27 mm in outer diameter; 52 mm in height). The solution in the vial was transferred to the shelf in the freeze-drying unit and frozen by cooling it at a temperature a little lower than −40° C. for 2 hours. The frozen solution was then dried under vacuum (0.1–0.01 torr) at the temperature as given in the table below. In the case of Experiment No. 3, the pressure in the drying chamber was kept to 0.15 torr. The temperature of the solution was controlled by adjusting the temperature of the shelf.

The results are given in the following Table:

| Experiment No. | Temperature of the solution (°C.) | Time required for completion of the drying | State of the dried Compound A |
|---|---|---|---|
| 1 | −25 | 2 days | well dried |
| 2 | −20 | 2 days | well dried |
| 3 | −16 | 1 day | well dried |

EXAMPLE 3

An aqueous solution of Compound A was freeze-dried in accordance with the following procedure:

Twelve ml of about 10 w/v % aqueous solution of Compound A was poured into a vial (25 ml in volume; 30 mm in outer diameter; 57 mm in height). The solution in the vial was transferred to the shelf in the freeze-drying unit and frozen by cooling it at a temperature a little lower than −40° C. for 2 hours. The frozen solution was then dried under vacuum (0.1–0.01 torr) at the temperature as given in the table below. In the case of Experiment No. 3, the pressure in the drying chamber was kept to 0.17 torr. The temperature of the solution was controlled by adjusting the temperature of the shelf.

The results are given in the following Table:

| Experiment No. | Temperature of the solution (°C.) | Time required for completion of the drying | State of the dried Compound A |
|---|---|---|---|
| 1 | −22 | 2 days | well dried |
| 2 | −17 | 2 days | well dried |
| 3 | −14 | 1 day | well dried |

EXAMPLE 4

An aqueous solution of Compound A was freeze-dried in accordance with the following procedure:

Twenty-four ml of about 10 w/v % aqueous solution of Compound A was poured into a vial (50 ml in volume; 40 mm in outer diameter; 60 mm in height). The solution in the vial was transferred to the shelf in the freeze-drying unit and frozen by cooling it at a temperature a little lower than −40° C. for 2 hours. The frozen solution was then dried under vacuum (0.1–0.01 torr) at the temperature as given in the table below. In the case of Experiment No. 3, the pressure in the drying chamber was kept to 0.17 torr. The temperature of the solution was controlled by adjusting the temperature of the shelf.

The results are given in the following Table:

| Experiment No. | Temperature of the solution (°C.) | Time required for completion of the drying | State of the dried Compound A |
|---|---|---|---|
| 1 | −28 | a little longer than 3 days | well dried |
| 2 | −22 | 3 days | well dried |
| 3 | −14 | 2 days | well dried |

EXAMPLE 5

An aqueous solution of Compound B was freeze-dried in accordance with the following procedure:

Three ml of about 10 w/v % aqueous solution of Compound B was poured into a vial (8 ml in volume; 21 mm in outer diameter; 40 mm in height). The solution in the vial was transferred to the shelf in the freeze-drying unit and frozen by cooling it at a temperature a little lower than −40° C. for 1½ hours. The frozen solution was then dried under vacuum (0.1–0.01 torr) at the temperature as given in the table below. The temperature of the solution was controlled by adjusting the temperature of the shelf.

The results are given in the following Table:

| Experiment No. | Temperature of the solution (°C.) | Time required for completion of the drying | State of the dried Compound B |
|---|---|---|---|
| 1 | −30 | 2 days | well dried |
| 2 | −25 | 1 day | well dried |
| 3 | −20 | 1 day | well dried |
| 4 | −15 | 1 day | well dried |
| 5 | −12 | 1 day | well dried |
| 6 | −8 | The solution melted during the drying process | |

EXAMPLE 6

An aqueous solution of Compound B was freeze-dried in accordance with the following procedure:

Eight ml of about 15 w/v % aqueous solution of Compound B was poured into a vial (18 ml in volume; 27 mm in outer diameter; 52 mm in height). The solution in the vial was transferred to the shelf in the freeze-drying unit and frozen by cooling it at a temperature a little lower than −40° C. for 2 hours. The frozen solution was then dried under vacuum (0.1–0.01 torr) at the temperature as given in the table below. In the case of Experiment No. 3, the pressure in the drying chamber was kept to 0.15 torr. The temperature of the solution was controlled by adjusting the temperature of the shelf.

The results are given in the following Table:

| Experiment No. | Temperature of the solution (°C.) | Time required for completion of the drying | State of the dried Compound B |
|---|---|---|---|
| 1 | −30 | 2 days | well dried |
| 2 | −20 | 1 day | well dried |
| 3 | −13 | 1 day | well dried |

EXAMPLE 7

An aqueous solution of Compound B was freeze-dried in accordance with the following procedure:

Twelve ml of about 20 w/v % aqueous solution of Compound B was poured into a vial (25 ml in volume; 30 mm in outer diameter; 57 mm in height). The solution in the vial was transferred to the shelf in the freeze-drying unit and frozen by cooling it at a temperature a little lower than −40° C. for 2 hours. The frozen solution was then dried under vacuum (0.1–0.01 torr) at the temperature as given in the table below. In the case of Experiment No. 4, the pressure in the drying chamber was kept to 0.17 torr. The temperature of the solution was controlled by adjusting the temperature of the shelf.

The results are given in the following Table:

| Experiment No. | Temperature of the solution (°C.) | Time required for completion of the drying | State of the dried Compound B |
|---|---|---|---|
| 1 | −30 | 3 days | well dried |
| 2 | −25 | 2 days | well dried |
| 3 | −17 | 1 day | well dried |
| 4 | −14 | 1 day | well dried |

What is claimed is:

1. In a process for freeze-drying an aqueous solution of a penicillin derivative of the formula:

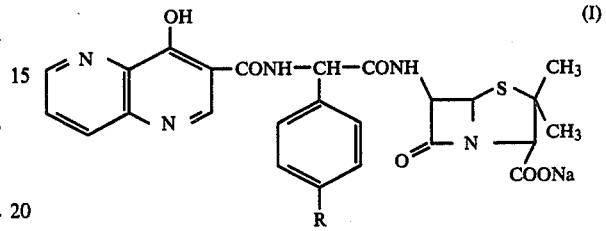

wherein R is a hydrogen atom or a hydroxyl group, by evaporating a frozen aqueous solution of the penicillin derivative (I) under vacuum from the frozen state to dryness, the improvement which comprises maintaining the temperature of the solution during the primary drying period of the drying process within a range from the eutectic point of the solution as determined by the electric resistance method to −8° C. when R is a hydrogen atom in said penicillin derivative, or from said eutectic point to −10° C. when R is a hydroxyl group in said penicillin derivative.

2. The process of claim 1, wherein R is a hydrogen atom and wherein the temperature of the solution during the primary drying period is maintained within a range from said eutectic point to −8° C.

3. The process of claim 1, wherein R is a hydroxyl group and wherein the temperature of the solution during the primary drying period is maintained within a range from said eutectic point to −10° C.

4. The process of claim 2, wherein the concentration of said penicillin derivative in the aqueous solution is from 5 w/v % to 12.5 w/v %.

5. The process of claim 3, wherein the concentration of said penicillin derivative in the aqueous solution is from 5 w/v % to 30 w/v %.

* * * * *